United States Patent
Schulten et al.

(10) Patent No.: US 6,230,573 B1
(45) Date of Patent: May 15, 2001

(54) DEVICE FOR SAMPLING GAS

(75) Inventors: Armin Schulten, Ahrensburg; Wolfgang Evers, Lübeck, both of (DE)

(73) Assignee: Drager Sicherheitstechnik GmbH (DE)

(*) Notice: Subject to any disclaimer, the term of this patent is extended or adjusted under 35 U.S.C. 154(b) by 0 days.

(21) Appl. No.: 09/401,689

(22) Filed: Sep. 22, 1999

(30) Foreign Application Priority Data

May 7, 1999 (DE) .......................................... 299 08 215 U

(51) Int. Cl.[7] .................................................. G01N 1/22
(52) U.S. Cl. .................... 73/863.86; 73/863.81; 422/86
(58) Field of Search ..................... 73/863.61, 863.71, 73/863.81, 863.86, 864.31, 864.33, 864.34; 422/55, 56, 57, 58, 60, 86

(56) References Cited

U.S. PATENT DOCUMENTS

| 3,653,429 | * | 4/1972 | Lawrence | 165/1 |
| 4,040,783 | * | 8/1977 | Collin | 23/232 |
| 4,159,304 | * | 6/1979 | Shono | 422/104 |
| 4,876,068 | * | 10/1989 | Castaneda | 422/58 |
| 4,915,296 | * | 4/1990 | Matsumoto et al. | 237/8 R |
| 4,947,696 | | 8/1990 | Fehlauer | 73/864.34 |
| 5,071,768 | * | 12/1991 | Klodowski | 436/39 |
| 5,081,871 | * | 1/1992 | Glaser | 73/863.23 |
| 5,139,746 | * | 8/1992 | Rabenecker | 422/104 |
| 5,179,024 | * | 1/1993 | Dahms | 436/42 |
| 5,305,658 | * | 4/1994 | Magee, Jr. | 73/864.82 |
| 5,538,690 | * | 7/1996 | Greer et al. | 422/86 |
| 5,670,119 | * | 9/1997 | Formica et al. | 422/104 |

OTHER PUBLICATIONS

Sensidyne, Inc., (registered), Universal Tube Holder System for Constant Low Flow & Constant–Pressure (Multi–Flow) Operation Instruction Manual, Doc. No. F–PRO–1218, Rev. B, Nov. 1996.*

* cited by examiner

Primary Examiner—Hezron Williams
Assistant Examiner—C D Garber
(74) Attorney, Agent, or Firm—McGlew and Tuttle, P.C.

(57) ABSTRACT

A device for gas sampling for gas analysis is provided which uses detector tubes. The device includes a test gas container with a gas inlet pipe, a gas outlet pipe, a mounting opening for the detector tube and with a break-off device for a detector tube tip located in the mounting opening. Nonreturn valves are provided on the gas inlet pipe and the gas outlet pipe. The closing bodies of the nonreturn valves are pressed by springs against corresponding valve seats and are held in a closed position, and are arranged in relation to one another such that a sample gas flow can be established from the gas inlet pipe to the gas outlet pipe.

8 Claims, 1 Drawing Sheet

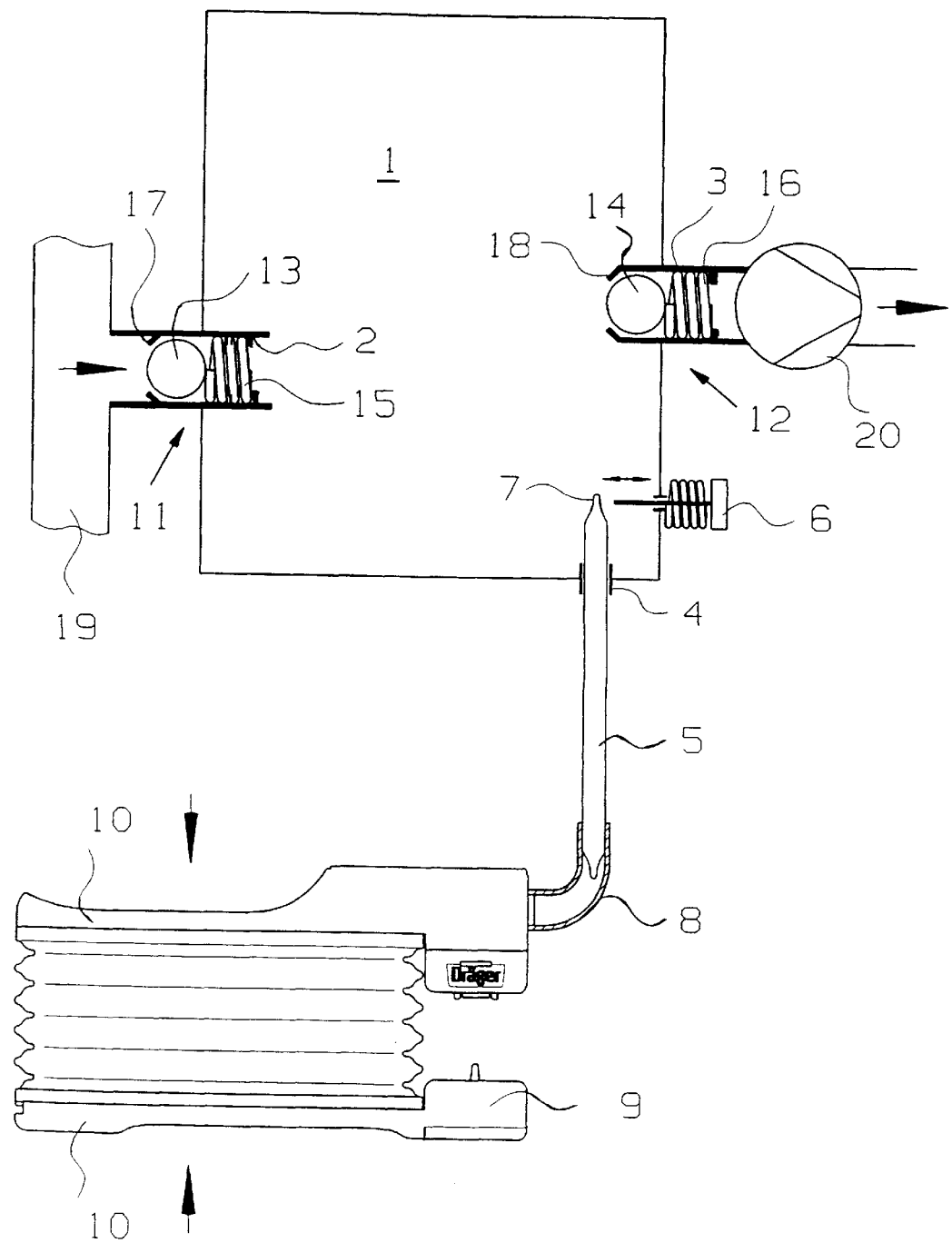

DEVICE FOR SAMPLING GAS

FIELD OF THE INVENTION

The present invention pertains to a device for sampling gas for gas analysis by means of detector tubes.

BACKGROUND OF THE INVENTION

In a glass tube, detector tubes contain a chemical preparation that reacts with the substance to be detected while undergoing a change in color, while the conversion of the substance is quantitatively displayed in the form of a color length display. For sampling, the gas tube is first opened by breaking off the tips of the detector tube on both sides. The detector tube is then placed into a sampling pump in order to draw a predetermined volume of the test gas through the detector tube. A sampling pump, with which a gas sample can be delivered through a detector tube stroke by stroke, has been known from DE 38 22 001.

However, the prior-art device for sampling gas cannot be used if very small amounts of substances that are also present in the ambient air atmosphere are to be detected. For example, a detector tube that is highly sensitive to water vapor must be used to detect water vapor in natural gas. If the tips of the detector tube are broken off only before the beginning of the measurement and the detector tube is placed into the sampling pump, the substance to be detected, which is present in the detector tube, is preloaded by the water vapor entering from the ambient atmosphere via the open tips of the detector tube such that measurement is no longer possible.

SUMMARY AND OBJECTS OF THE INVENTION

The primary object of the present invention is to improve a device of the above-described type such that gas analysis is possible without the influence of gas components from the ambient atmosphere.

According to the invention a device for gas sampling for gas analysis using detector tubes is provided including a test gas container with a gas inlet pipe, a gas outlet pipe, a mounting opening for the detector tube and with a break-off device for a detector tube tip located in the mounting opening. Nonreturn valves are provided on the gas inlet pipe and the gas outlet pipe. The closing bodies of the nonreturn valves are pressed by springs against corresponding valve seats and are held in a closed position, and are arranged in relation to one another such that a sample gas flow can be established from the gas inlet pipe to the gas outlet pipe.

The advantage of the present invention is essentially that by arranging the detector tube on a test gas container, through which sample gas flows, and by breaking off the tip of the detector tube under the atmosphere of the sample gas, effects of the ambient air on the substance to be detected are completely prevented from occurring. The gas sampling takes place such that the gas inlet pipe is connected to the gas source to be analyzed and the gas outlet pipe is connected to a gas delivery pump. The nonreturn valves located in the pipes open due to the vacuum applied by the gas delivery pump and the gas sample flows through the test gas container. The detector tube is then placed into the mounting opening located on the test gas container. The tip of the detector tube located within the mounting opening is removed by pressing the break-off device. The other end of the detector tube is then connected to a sampling pump, and the second tip of the detector tube is then opened, e.g., with another break-off device located on the sampling pump. The sample volume corresponding to the detector tube can now be drawn through the detector tube.

The gas sampling may be performed either with or without flow through the test gas container, and a site-independent measurement is also possible in the case of a test gas container with flow through, because the nonreturn valves close after interruption of the suction process or after the test gas container has been uncoupled from the sampling source and the gas delivery pump, so that no gas can penetrate into the interior space of the test gas container from the outside.

The spring force acting on the closing body of the nonreturn valve at the gas inlet pipe is advantageously selected to be such that it is stronger than the maximum suction force that can be applied by the sampling pump. It is achieved as a result that no foreign gas can be drawn into the test gas container from the environment by means of the sampling pump in the case of a site-independent measurement. A sampling pump with a detector tube has been known from U.S. Pat. No. 4,947,696 which is hereby incorporated by reference.

With a test gas container of a specifically defined volume, e.g., 100 mL, the sample volume can be limited to less than 100 mL. In the case of measurement at the test gas container with the valves closed, sample is taken only until the vacuums in the test gas container and in the sampling pump become equal. As a result, it is possible to use even smaller sample volumes for the measurement of very high pollutant concentrations.

One exemplary embodiment of the present invention is shown in the figure and will be explained in greater detail below.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

In the drawings:

The only FIGURE is a schematic partially sectional view of the device of the invention.

DESCRIPTION OF THE PREFERRED EMBODIMENT

Referring to the drawing in particular, the FIGURE schematically shows a test gas container 1 with a gas inlet pipe 2, a gas outlet pipe 3, a mounting opening 4 for the detector tube 5, and a break-off device 6 for the tip 7 of the detector tube. The other end of the detector tube 5 is connected via a flexible tube 8 to a sampling pump 9, whose grip plates 10 can be pressed together for sampling gas.

Nonreturn valves 11, 12, whose closing bodies 13, 14 are pressed by means of springs 15,16 against the corresponding valve seats 17, 18, are located in the pipes 2, 3. The nonreturn valves 11, 12 are arranged within the pipes 2, 3 such that only a sample gas flow is possible from the gas inlet 2 to the gas outlet 3.

The gas inlet 2 is connected to a sampling source 19, e.g., a natural gas source, while the gas outlet pipe 3 is connected to a gas delivery pump 20.

Water vapor in natural gas is to be detected with the device according to the present invention, e.g., during gas sampling on a drilling rig.

The measurement takes place such that the gas delivery pump 20 is first switched on and natural gas is drawn in from the sampling source 19. After sufficient scavenging of the test gas container 1, the unopened detector tube 5 is placed with one side into the mounting opening 4, while the other side is connected to the sampling pump 10 via a flexible tube 8. The tips of the detector tube are subsequently removed by means of the break-off device 6 and by pressure on the flexible tube 8. The gas sampling can now be carried out by pressure on the grip plates 10 according to the measuring instructions of the detector tube 5.

In the case of site-independent gas analysis, the sampling source 19 and the gas delivery pump 20 are separated from the test gas container, and the nonreturn valves 11, 12 will close automatically. Site-independent measurement may be necessary when the gas sampling can be carried out under difficult conditions only and no detector tube 5 can be used for the gas analysis on the site.

While a specific embodiment of the invention has been shown and described in detail to illustrate the application of the principles of the invention, it will be understood that the invention may be embodied otherwise without departing from such principles.

What is claimed is:

1. A device for gas sampling for gas analysis using a detector tube, the device comprising:
    a test gas container with a gas inlet, a gas outlet, a mounting opening for the detector tube and with a break-off device for breaking off a detector tube tip located in said mounting opening;
    a gas inlet nonreturn valve having an inlet valve seat, an inlet valve closing body and an inlet valve spring, said inlet valve spring pressing said inlet valve closing body against said inlet valve seat to hold said inlet valve closing body in a closed position; and
    a gas outlet nonreturn valve having an outlet valve seat, an outlet valve closing body and an outlet valve spring, said outlet valve spring pressing said outlet valve closing body against said outlet valve seat to hold said outlet valve closing body in a closed position, said gas inlet nonreturn valve being arranged in relation to said gas outlet nonreturn valve such that a sample gas flow can be established from said gas inlet pipe to the said gas outlet pipe.

2. The device in accordance with claim 1, further comprising: a gas sampling pump, wherein a spring force of said inlet valve spring acting on said inlet valve closing body is selected to be stronger than the suction force of said sampling pump connected to the said detector tube.

3. The device in accordance with claim 1, wherein each of said gas inlet nonreturn valve and said gas outlet nonreturn valve are ball seat valves.

4. The device in accordance with one of the claim 1, further comprising a gas delivery pump, wherein said gas inlet is provided as a pipe that can be connected to a sampling source and said gas outlet is a pipe with a gas delivery pump connection.

5. A gas sampling arrangement for gas analysis, the arrangement comprising:
    a detector tube with a first detector tube tip and a second detector tube tip;
    a test gas container with a gas inlet, a gas outlet, a mounting opening for the detector tube and with a break-off device for breaking off said first detector tube tip with said detector tube having an end located in said mounting opening;
    a gas inlet nonreturn valve having an inlet valve seat, an inlet valve closing body and an inlet valve spring, said inlet valve spring pressing said inlet valve closing body against said inlet valve seat to hold said inlet valve closing body in a closed position;
    a gas outlet nonreturn valve having an outlet valve seat, an outlet valve closing body and an outlet valve spring, said outlet valve spring pressing said outlet valve closing body against said outlet valve seat to hold said outlet valve closing body in a closed position, said gas inlet nonreturn valve being arranged in relation to said gas outlet nonreturn valve such that a sample gas flow can be established from said gas inlet pipe to the said gas outlet pipe;
    a flexible tube connected to an end of said detector tube adjacent to said second detector tube tip, whereby pressure on said flexible tube is used to remove said second detector tube tip; and
    a gas sampling pump connected to said flexible tube.

6. The arrangement in accordance with claim 5, wherein a spring force of said inlet valve spring acting on said inlet valve closing body is selected to be stronger than the suction force of said sampling pump connected to the said detector tube.

7. The arrangement in accordance with claim 5, wherein each of said gas inlet nonreturn valve and said gas outlet nonreturn valve are ball seat valves.

8. The arrangement in accordance with one of the claim 5, further comprising a gas delivery pump, wherein said gas inlet is provided as a pipe that can be connected to a sampling source and said gas outlet is a pipe with a gas delivery pump connection.

\* \* \* \* \*